(12) United States Patent
Szucs

(10) Patent No.: US 8,545,455 B2
(45) Date of Patent: Oct. 1, 2013

(54) NEEDLE SHIELD FOR INJECTIONS

(75) Inventor: Sarah W. Szucs, Geneseo, NY (US)

(73) Assignee: University of Rochester, Rochester, NY (US)

(*) Notice: Subject to any disclaimer, the term of this patent is extended or adjusted under 35 U.S.C. 154(b) by 357 days.

(21) Appl. No.: 12/749,008

(22) Filed: Mar. 29, 2010

(65) Prior Publication Data

US 2010/0249748 A1 Sep. 30, 2010

Related U.S. Application Data

(60) Provisional application No. 61/164,661, filed on Mar. 30, 2009.

(51) Int. Cl.
*A61M 5/32* (2006.01)
(52) U.S. Cl.
USPC .......................................... 604/198; 604/506
(58) Field of Classification Search
USPC .................................. 604/110, 189, 192, 198
See application file for complete search history.

(56) References Cited

U.S. PATENT DOCUMENTS

| | | | | |
|---|---|---|---|---|
| 3,134,380 A | * | 5/1964 | Armao | 604/198 |
| 5,429,611 A | * | 7/1995 | Rait | 604/197 |
| 5,865,804 A | | 2/1999 | Bachynsky | |
| 5,964,731 A | * | 10/1999 | Kovelman | 604/110 |
| 6,884,224 B2 | * | 4/2005 | Dalton | 600/573 |
| 6,945,952 B2 | | 9/2005 | Kwon | |
| 7,041,086 B2 | * | 5/2006 | Yang | 604/198 |
| 7,182,747 B2 | | 2/2007 | Kwon | |
| 7,182,749 B2 | | 2/2007 | Heiniger et al. | |
| 7,326,185 B2 | | 2/2008 | Brand et al. | |
| 2003/0168366 A1 | * | 9/2003 | Hirsiger et al. | 206/365 |
| 2005/0209567 A1 | * | 9/2005 | Sibbitt | 604/187 |

FOREIGN PATENT DOCUMENTS

| | | |
|---|---|---|
| WO | 00/30705 | 6/2000 |
| WO | 2007/026164 | 3/2007 |

OTHER PUBLICATIONS

Cox, Darcy, and Stone, Jerome; "Managing Self-Injection Difficulties in Patients with Relapsing-remitting Multiple Sclerosis"; J Neurosci Nurs. 2006; 38(3): 161-171; 2006 American Association of Neuroscience Nurses; Posted to www.medscape.com/viewarticle/548016 Dec. 20, 2006; 7 pages.
Scwartz, Ph.D., LCSW, Allan; "Blenophobia, The Fear of Needles", posted to www.mentalhealth.net/poc/view doc.php?type=weblog&wlid=5&id=405&cn=1 Apr. 28, 2008; 3 pages.
Thompson, "New-Generation Auto-Injectors: Completing the Scale of Convenience for Self-Injection," Technology Overviews, published prior to Mar. 20, 2010, 3 pages.

(Continued)

*Primary Examiner* — Emily Schmidt
(74) *Attorney, Agent, or Firm* — Blank Rome LLP

(57) ABSTRACT

A needle shield for hiding a needle from a patient during an injection is disclosed. The needle shield comprises an attaching portion for attaching the needle shield to a syringe and an opaque collapsible element extending from the attaching portion, the collapsible element having an orifice extending therethrough and being of a sufficient length to conceal a needle from view when the needle is disposed in the orifice, and wherein the collapsible element collapses and conceals the needle as the needle is inserted into a patient's skin and expands to retain its original shape as the needle is withdrawn from the patient's skin so that the patient does not see the needle during an injection.

10 Claims, 2 Drawing Sheets

(56) References Cited

OTHER PUBLICATIONS

Author Unknown, "Owen Mumford—Automatic Injection Pens and Auto Injectors for Self-Injection," published prior to Mar. 20, 2010, 2 pages, posted to www.pharmaceutical-technology.com/contractors/drug_delivery/owen.

Author Unknown, "BD Prefillable Self-Injection Systems," published prior to Mar. 20, 2010, 2 pages, posted to www.bd.com/pharmaceuticals/products/self-injection.asp.

* cited by examiner

US 8,545,455 B2

NEEDLE SHIELD FOR INJECTIONS

RELATED APPLICATIONS

The present application claims the benefit of U.S. Provisional Application Ser. No. 61/164,661, filed Mar. 30, 2009, the disclosure of which is incorporated herein in its entirety by reference.

FIELD OF THE INVENTION

The present invention relates to a new and useful method and device for relieving the apprehension and anxiety associated with the sight of a needle piercing the skin during injections. More particularly, the present invention relates to a new and useful method and device for providing a shield to obscure the sight of a needle piercing one's skin/flesh during injections.

BACKGROUND OF THE INVENTION

Needle sticks are a vital part of the practice of medicine. Needle sticks are used to perform routine diagnostic procedures, such as tests for cholesterol levels, infections, blood count, and blood type. Needle sticks are also used to give injections for treating various diseases and medical conditions, such as administering vaccines and antibiotics. Accordingly, an inability to receive needle sticks can pose a serious threat to an individual's health.

Fear of needles, or Blenophobia, is known to increase the sense of pain during needle sticks. Many of the physical reactions associated with Blenophobia are initiated by watching the needle piercing the individual's skin. The fear associated with Blenophobia may result in such a fearful reaction to needles that an individual can no longer tolerate going anywhere near doctors' offices. In fact, an estimated 20 million Americans a year avoid going to the doctor because of a fear of needle sticks. Avoiding medical visits can be quite dangerous for individuals experiencing symptoms that indicate conditions or diseases requiring medical attention.

In addition, treatment regimens that require more frequent injections are more likely to be associated with Blenophobia. Such treatment regimens include those for multiple sclerosis (MS) and diabetes. And, unfortunately, the frequency of injections required by those treatment regimens also typically dictates that an individual self-inject. Such self-injections allow patients to reduce the risk of missed injections and to increase their independence from medical facilities. Thus, Blenophobia can prevent adherence to critical treatment regimens. Accordingly, there is a need for a new and useful method and device for relieving the apprehension and anxiety associated with the sight of a needle piercing the skin during injections.

SUMMARY OF THE INVENTION

Accordingly, to solve at least the above problems and/or disadvantages and to provide at least the advantages described below, a non-limiting object of the present invention is to provide a needle shield for hiding a needle from a patient during an injection comprising an attaching portion for attaching the needle shield to a syringe and an opaque collapsible element extending from the attaching portion, the collapsible element having an orifice extending therethrough and being of a sufficient length to conceal a needle from view when the needle is disposed in the orifice, and wherein the collapsible element collapses and conceals the needle as the needle is inserted into a patient's skin and expands to retain its original shape as the needle is withdrawn from the patient's skin so that the patient does not see the needle during an injection.

BRIEF DESCRIPTION OF THE DRAWINGS

Many aspects of the present invention can be better understood with reference to the following drawings, which are part of the specification and represent preferred embodiments of the present invention. The components in the drawings are not necessarily to scale, emphasis instead being placed upon illustrating the principles of the present invention. And, in the drawings, like reference numerals designate corresponding parts throughout the several views.

DETAILED DESCRIPTION OF THE INVENTION

Figure 1:
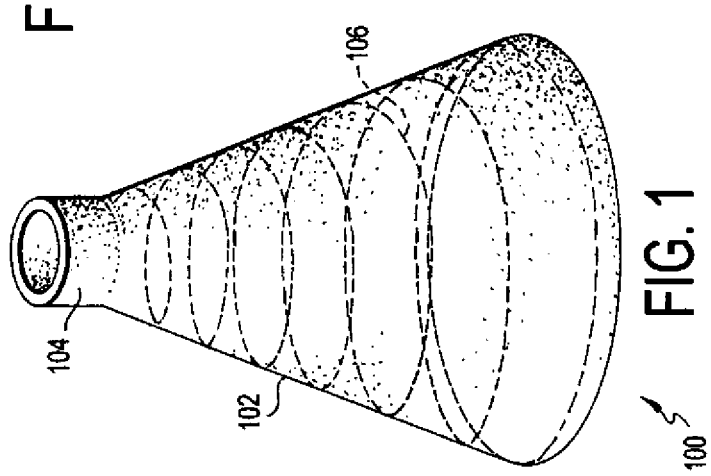
FIG. 1 is an orthogonal view illustrating a non-limiting exemplary embodiment of a needle shield according to the present invention.

Reference will now be made in detail to non-limiting embodiments of the present invention by way of reference to the accompanying drawings, wherein like reference numerals refer to like parts, components, and structures.

Figure 2:
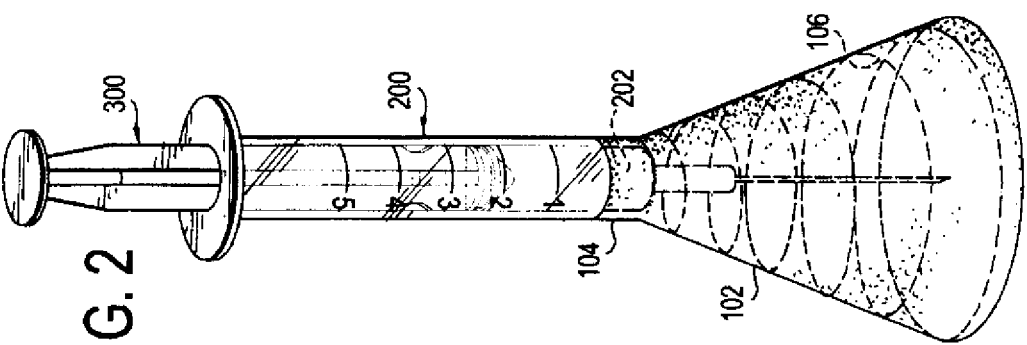
FIG. 2 is an orthogonal view illustrating the needle shield of FIG. 1 installed on a syringe prior to inserting a needle into a patient's skin.

The present invention addresses at least the problems described above by providing a shield 100 that conceals the needle at the end of a syringe at all times during an injection. The non-limiting exemplary embodiment of the shield 100 illustrated in FIG. 1 includes a cone-shaped needle-covering portion 102 that includes an orifice extending therethrough that is configured to receive a needle wholly therein. At the top of the needle-covering portion 102 is a substantially cylindrical attaching portion 104 that is configured to fit over the cylindrical base/hub 202 of a standard syringe 200 and attach the shield 100 thereto (FIG. 2). The needle-covering portion 102 also includes a thin wire 106 disposed therein in a substantially spiral shape to give the needle-covering portion 102 its conical shape. The wire is formed from a resilient material, such as metal or a flexible plastic, to allow the needle-covering portion 102 to be compressed and flattened under pressure and to retain its conical shape when the pressure is removed. The needle-covering portion 102 is of sufficient length to shield the needle of a syringe from view at all times during an injection. Accordingly, the needle-covering portion 102 may be the same length as a subcutaneous needle or an intramuscular (IM) needle (e.g., ½ inch to 1½ inches), but can also be sized smaller to fit over the needles of insulin and heparin syringes.

The needle-covering portion 102 may be formed from a sterile, flexible, latex-free material. The material is necessarily opaque so that a needle cannot be seen through it. The needle-covering portion 102 may also be made of a resilient latex-free material that provides the same functionality as the thin wire 106 so the thin wire 106 is not required. Or, the needle-covering portion 102 may be formed entirely from the thin wire 106 such that the thin wire 106 forms an enclosed spring element that shields the needle from view.

As FIG. 2 illustrates, the shield 100 is configured to attach to a syringe 200 by sliding the attaching portion 104 over the base/hub 202 of the syringe 200. The attaching portion 104 is configured with a tolerance to provide an interference fit with the base/hub 202 of the syringe 200 so that the shield 100 remains attached and in place on the syringe 200 when installed. In the alternative, the attaching portion 104 may be configured with any suitable attaching mechanism, such as threads for engaging corresponding threads on the base/hub 202 of the syringe 200, so that the shield 100 remains attached and in place on the syringe 200 when installed.

Figure 3:
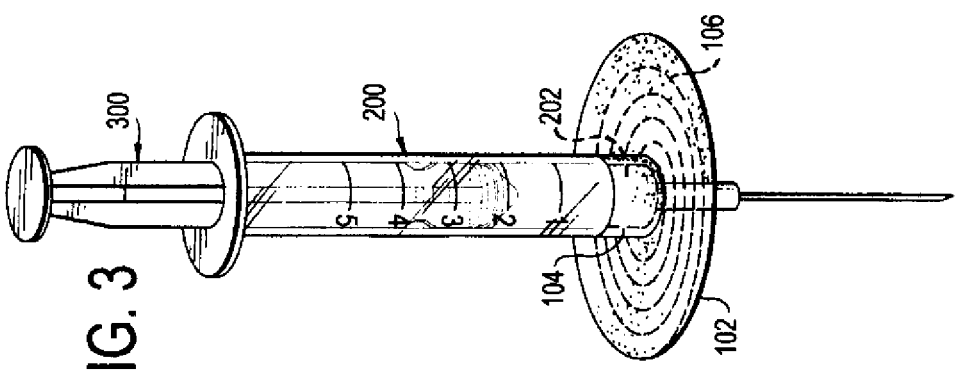
FIG. 3 is an orthogonal view illustrating the needle shield of FIG. 1 installed on a syringe with the needle fully inserted into a patient's skin.

In use, a patient places the shield 100 against the area of the skin to which an injection is to be administered and asserts downward pressure on the syringe 200 until the needle-covering portion 102 of the shield 100 collapses. As FIG. 3 illustrates, the needle is inserted up to the syringe hub 202 such that the needle-covering portion 102 of the shield 100 collapses up to the hub 202, and the lower edge of the needle-covering portion 102 extends radially outward until the needle-covering portion 102 takes the shape of a substantially flat circle that is substantially wider than the attaching portion 104. When the needle-covering portion 102 of the shield 100 is substantially flat, the patient will know that the needle of the syringe 200 is completely inserted, and the patient can inject the dose of medicine in the syringe 200 by depressing the plunger 300 on the syringe 200. After the dose of medicine is injected, the resilient nature of the thin wire 106 will produce a spring like effect to assist in withdrawing the needle from the patient's skin and to re-form the needle-covering portion 102 in a substantially conical shape as the needle is withdrawn, which maintains the needle shielded from the patient's view as it is withdrawn. And, after the needle is withdrawn from the patient's skin, the needle-covering portion 102 will also cover the needle sufficiently to prevent any potential needle stick injuries in the patient, caregiver or health care practitioner.

After use, the entire syringe 200, needle, and shield 100 may be disposed of together in a sharps container. Or, if the shield 100 is provided on a re-usable syringe, such as a pen injector, the shield 100 can be re-used for subsequent injections. Depending on the application, the shield 100 may be attached to the syringe 200 separately from the needle so that the cap can be removed from the needle and medicine can be withdrawn from a vial without interference from the shield 100. Or, the shield 100 may be provided with the needle and attached to the syringe 200 at the same time when the syringe 200 already has the required medicine in it, such as with auto-injectors.

Figure 4:
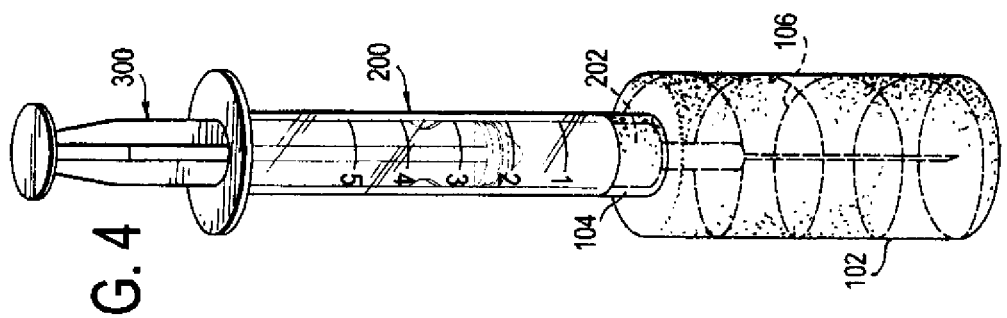
FIG. 4 is an orthogonal view illustrating another non-limiting exemplary embodiment of a needle shield according to the present invention, installed on a syringe prior to inserting a needle into a patient's skin.
Figure 8:
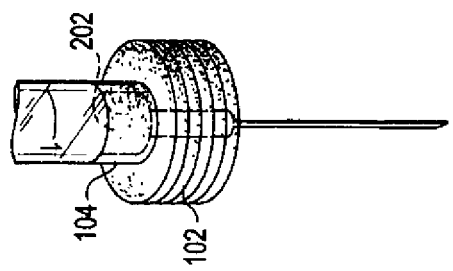
FIG. 8 is an orthogonal view illustrating the needle shield of FIG. 7 installed on a syringe with the needle fully inserted into a patient's skin.
Figure 7:
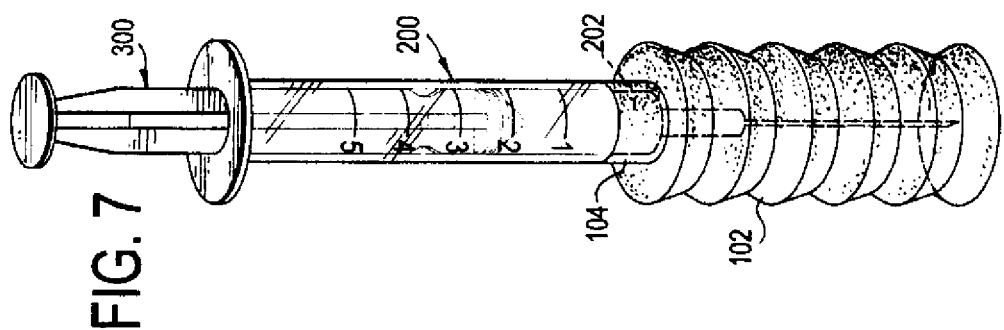
FIG. 7 is an orthogonal view illustrating still yet another non-limiting exemplary embodiment of a needle shield according to the present invention, installed on a syringe prior to inserting a needle into a patient's skin.
Figure 6:
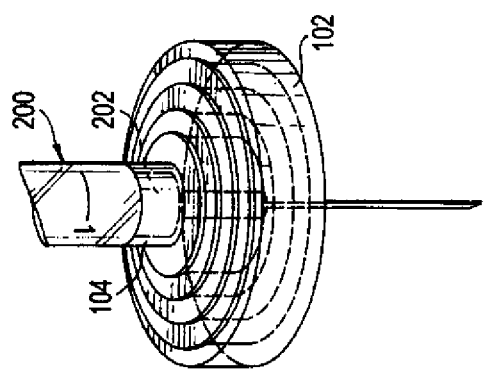
FIG. 6 is an orthogonal view illustrating the needle shield of FIG. 5 installed on a syringe with the needle fully inserted into a patient's skin.
Figure 5:
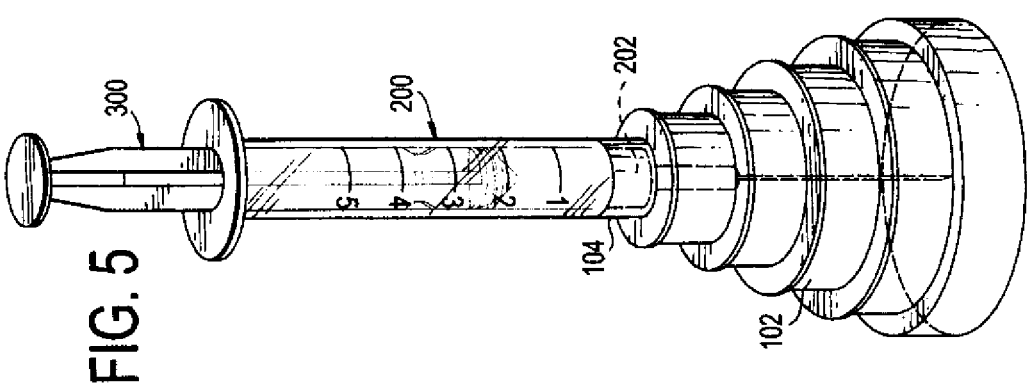
FIG. 5 is an orthogonal view illustrating yet another non-limiting exemplary embodiment of a needle shield according to the present invention, installed on a syringe prior to inserting a needle into a patient's skin.

As illustrated in FIGS. 4-8, the needle-covering portion 102 of the shield 100 may also have other shapes and/or configurations without departing from the spirit of the present invention. As illustrated in FIG. 4, the needle-covering portion 102 may be a substantially cylindrical in shape while functioning in a substantially similar manner as the cone-shaped needle-covering portion 102 illustrated in FIGS. 1-3. Or, as illustrated in FIGS. 5 and 6, the needle-covering portion 102 may be substantially cylindrical in shape and configured to collapse and expand in a telescoping manner, wherein progressively wider concentric cylindrical portions are sequentially fitted in slidable engagement with one another and each preceding sequential cylindrical portion can be collapsed into or expanded from the widest cylindrical portion in a telescoping manner. Or, as illustrated in FIGS. 7 and 8, the needle-covering portion 102 may be substantially cylindrical in shape and configured to collapse and expand like a bellows at a plurality of consecutive parallel circular folds along the perimeter of the needle-covering portion 102. In the embodiments illustrated in FIGS. 5-8, a resilient spring wire 106 is not shown but may also be provided to assist in expanding either of those needle-covering portions 102 back to their respective expanded shapes.

The needle-covering portion 102 of the shield 100 may be provided with a design on the external surface that changes as the needle-covering portion 102 flattens out into a circle as the needle is inserted into the patient's skin. The change in pattern can be used to indicate to a patient when the needle is completely in the skin. That design can include cheerful and uplifting pictures to further relax the patient during an injection.

Accordingly, the shield 100 of the present invention eases the fear of needles by concealing the needle from a patient's view during an injection. The shield can be used for self-injections as well as when the patient is receiving an injection form a caregiver, such as in a pediatric setting in doctors offices, acute care, and home care. Thus, the shield 100 provides a novel solution for addressing a patient's fear of needles, such as in a patient with Blenophobia. Moreover, by covering the needle at all times during an injection, the shield 100 protects the user from the needle after an injection as the user disposes of the needle and/or syringe 200.

The foregoing description and drawings should be considered as illustrative only of the principles of the invention. The invention may be configured in a variety of shapes and sizes and is not intended to be limited by the preferred embodiment. Numerous applications of the invention will readily occur to those skilled in the art. Therefore, it is not desired to limit the invention to the specific examples disclosed or the exact construction and operation shown and described. Rather, all suitable modifications and equivalents may be resorted to, falling within the scope of the invention.

What is claimed is:

1. A needle shield for injections comprising:
    an attaching portion for attaching the needle shield to a syringe; and
    an opaque collapsible element extending from the attaching portion, the collapsible element having an orifice extending therethrough and being of a sufficient length to conceal a needle from view when the needle is disposed in the orifice, and the collapsible element having a substantially conical shape,
    wherein the collapsible element collapses such that the collapsible element is substantially wider than the attaching portion and conceals the needle as the needle is inserted into a patient's skin and expands to retain its original shape as the needle is withdrawn from the patient's skin so that the patient does not see the needle during an injection.

2. The needle shield of claim 1, wherein the collapsible element includes a resilient spring member to re-form the collapsible member into the at least one of a conical shape and a cylindrical shape as the needle is withdrawn from the patient's skin.

3. The needle shield of claim 2, wherein the resilient member is a helical spring.

4. The needle shield of claim 1, wherein the collapsible element is made of a resilient latex-free material that will collapse and expand without the use of a spring.

5. The needle shield of claim 1, wherein the attaching portion is configured to attach to the syringe via threaded engagement.

6. A method of giving an injection comprising:
filling a syringe with a compound to be injected, the syringe having a needle shield with an attachment portion and an opaque collapsible element extending therefrom to conceal a needle of the syringe from view when the needle is disposed therein, the collapsible element having a substantially conical shape;
and
collapsing and compressing the collapsible element as the needle is inserted into a patient's skin, such that the collapsible element is substantially wider than the attaching portion, and expanding the collapsible element to retain its original shape as the needle is withdrawn from the patient's skin so that the patient does not see the needle during the injection.

7. The method of claim 6, wherein the step of collapsing the collapsible element includes compressing a resilient spring member that expands to re-form the collapsible member into the conical shape as the needle is withdrawn from the patient's skin.

8. The method of claim 7, wherein the resilient member is a helical spring.

9. The method of claim 6, wherein the step of collapsing the collapsible element includes compressing a resilient latex-free material that expands to re-form the collapsible member into its substantially conical shape as the needle is withdrawn from the patient's skin without the use of a spring.

10. The method of claim 6, further comprising the step of attaching the collapsible element to the syringe via threaded engagement.

* * * * *